United States Patent [19]
Delley et al.

[11] Patent Number: 5,429,924
[45] Date of Patent: * Jul. 4, 1995

[54] DNA PROBE FOR LACTOBACILLUS DELBRUECKII

[75] Inventors: Mich',acu/e/ le Delley, Savigny; Herbert Hottinger, Blonay; Beat Mollet, Mollie-Margot, all of Switzerland

[73] Assignee: Nestec S.A., Vevey, Switzerland

[*] Notice: The portion of the term of this patent subsequent to Oct. 25, 2011 has been disclaimed.

[21] Appl. No.: 51,190

[22] Filed: Apr. 22, 1993

Related U.S. Application Data

[63] Continuation of Ser. No. 494,139, Mar. 14, 1990, Pat. No. 5,359,049.

[30] Foreign Application Priority Data

Apr. 6, 1989 [EP] European Pat. Off. ............ 89106016
Feb. 10, 1990 [EP] European Pat. Off. ............ 90102651

[51] Int. Cl.$^6$ .................... C12Q 1/68; C07H 15/12; C12N 15/00
[52] U.S. Cl. ..................... 435/6; 536/24.32; 435/320.1
[58] Field of Search .................. 435/6, 320.1; 536/24.32

[56] References Cited

PUBLICATIONS

J. Jagow, et al., Enumeration by DNA Colony Hybridization of Virulent Yersinia enterocolitica Colonies in Artifically Contaminated Food. Appl. Environ. Microbiol. vol. 51, No. 2, pp. 441–443 (1986).
R. H. Barker, Jr., et al., Specific DNA Probe for the Diagnosis of Plasmodium falciparum Malaria. Science 231, pp. 1434–1436 (1986).
F. A. Rubin, et al., Development of a DNA Probe to Detect Salmonella typhi. J. Clin. Microbiol. vol. 22, No. 4, pp. 600–605 (1985).
J. Kraus, et al., A cloned 23SrRNA gene fragment of Bacillus subtilis and its use as a hybrization probe of conserved character. FEMS Microbiol. Lett. 33 pp. 89–93 (1986).
F. Malouin, et al., DNA Probe Technology for Rapid Detection of Haemophilus influenzae in Clinical Specimens. J. Clin. Microbiol. vol. 26, No. 10, pp. 2132–2138 (1988).
J. Brandsma, et al., Nucleic acid spot hybridization: Rapid quantitative screening of lymphoid cell lines for Epstein–Barr viral DNA. Proc. Natl. Acad. Sci. USA vol. 77, No. 11, pp. 6851–6855 (1980).
P. Stålhandske, et al., Identification of DNA Viruses by Membrane Filter Hybrization. J. Clin. Microbiol. vol. 15, No. 4, pp. 744–747 (1982).
P. Stålhandske, et al., Detection of Adenoviruses in Stool Specimens by Nucleic Acid Spot Hybridization. J. Med. Virol., 16: pp. 213–218 (1985).
J. Flores et al., A Dot Hybridisation Assay for Detection of Rotavirus. The Lancet, 555–559 (1983).
M. Lin, et al., Diagnosis of Rotavirus Infection with cloned cDNA Copies of Viral Gerome Segments. J. Virol. vol. 55, No. 2, 509–512 (1985).
H. A. R. Petrick, et al., Isolation of a DNA Probe for Lactobacillus Curvatus. Appl. Environ. Microbiol. vol. 54, No. 2, 405–408 (1988).
Saiki, et al., Enzymatic Amplification of $\beta$-Globin Genomic Sequences and Restriction Site Analysis for Diagnosis of Sickle Cell Anemia Science, vol. 230, 1350–1354 (1985).
Saika, et al., Primer–Directed Enzymatic Amplification of DNA with a Thermostable DNA Polymerase. Science, vol. 239, pp. 487–491 (1988).

(List continued on next page.)

Primary Examiner—Mindy B. Fleisher
Attorney, Agent, or Firm—Vogt & O'Donnell

[57] ABSTRACT

Strains of the Lactobacillus delbrueckii species are identified and distinguished from other species by a DNA probe containing an EcoRI fragment, or subfragment thereof, of the plasmid pY85, which hybridizes specifically to chromosomal DNA of strains of the L. delbrueckii species.

8 Claims, 1 Drawing Sheet

PUBLICATIONS

H. W. Boyer, et al., A Complementation Analysis of the Restriction and Modification of DNA in *Escheria coli*. J. Mol. Biol. 41, pp. 459–472 (1988).

H. Hottinger, et al., Nonsense Suppression in Schizosaccharomyces pombe: The S. pombe Sup 3–e tRNA gene is active S. Cerevisiae. Mol. Gen. Genet. 188, pp. 219–224 (1982).

E. M. Southern, Detection of Specific Sequences Among DNA Fragments Separated by Gel Electrophoresis. J. Biol. 98, pp. 503–517 (1975).

F. Sanger, et al., A Rapid Method for Determining Sequences in DNA by Primed Synthesis with DNA Polymerase. J. Mol. Biol. 94, pp. 441–448 (1975).

F. Sanger, et al., DNA Sequencing with chain-terminating inhibitors. Proc. Natl. Acad. Sci. vol. 74, No. 12, pp. 5463–5467 (1977).

J. Messing, et al., A new pair of M13 vectors for selecting either DNA strand of double–digest restriction fragments. Gene, 19, pp. 269–276 (1982).

M. C. Zwahlen, et al., Nucleotide sequence of a Lactobacillus delbrueckii gene encoding a minor (UCG) tRNA Ser. Nucleic Acids Research. vol. 17, No. 4 (1989).

H. Hottinger, et al., A llele–specific complementation of an *Escherichia coli* leu$\beta$ mutation by a Lactobacillus bulgaricus tRNA gene. Gene, vol. 60, pp. 75–83 (1987).

Chemical Abstracts, No. 100: 115815 V (1984).

Tannock, Biotin–Labeled Plasmid DNA for Detection of Epithelium–Associated strains of Lactobacilli. Appl. Environ. Microbiol. vol. 55, No. 2, pp. 461–464 (1989).

Maniatis, et al., Molecular Cloning, A Laboratory Manual, Cold Spring Habor Laboratory. 1982 pp. 117–121.

DNA PROBE FOR LACTOBACILLUS DELBRUECKII

This application is a continuation of Ser. No. 07/494,139, filed Mar. 14, 1990 now U.S. Pat. No. 5,359,049.

BACKGROUND OF THE INVENTION

The present invention relates to a DNA probe for identifying bacterial strains of the *Lactobacillus delbrueckii* species, a process for producing such a probe and methods for identifying bacterial strains of this species with this DNA probe.

*Lactobacillus delbrueckii* subsp. *bulgaricus, delbrueckii* and *lactis* are very important bacteria for the fermentation of food. *L.bulgaricus* and *L.lactis* are predominantly used in fermentation of milk products and are therefore found in starter cultures for yoghurt and cheese production, whereas *L.delbrueckii* is mainly found in vegetable fermentations. Fermentation and maturation of these food products usually result from growth association and interaction of different bacteria, in most cases different Lactobacilli, Lactococci and other bacterial species. As most of these bacterial species have very similar nutritional requirements and grow under similar environmental conditions a clear identification within the Lactobacillus species is sometimes very difficult. So far the classification of these species is very tedious and involves many unreliable criteria like sugar fermentation patterns and acid production. Due to these tests, a differentiation of different species remains difficult, sometimes doubtful and often arbitrary.

DNA hybridisation techniques, using specific DNA probes, are a very valuable tool for the identification of bacterial and viral strains and have already found application in clinical diagnostics. Such DNA probes have already been used for the identification of *Yersinia enterocolitica* (J.Jagow et al., Appl. Environ. Microbiol. 51, 441–443, 1986), *Plasmodium falciparum* (R. H. Barker et al,. Science 231, 1434–1436, 1986), *Salmonella typhi* (F. A. Rubin et al., J.Clin.Microbiol. 22, 600–605, 1985), *Bacillus subtilis* (J.Krauss et al., FEMS Microbiol. Lett. 33, 89–93, 1986), *Haemophilus influenzae* (F. Malouin et al., J. Clin. Microbiol. 26, 2132–2138, 1988) and other bacterial species, of DNA viruses (J.Brandsma et al., Proc.Natl. Acad. Sci.USA 77, 6851–6855; P.Stolhandske et al., J.Clin.Microbiol. 15, 744–747, 1982; P.Stolhandske et al., J.Med.Virol. 12, 213–218,1985), as well as RNA viruses (J.Flores et al., Lanceti, 555–559, 1983; M. Lin et al., J. Virol. 55, 509–512, 1985).

In the species of Lactobacillus, only a probe for *L.curvatus* (H.A.R.Petrick et al, Appl.Environ.Microbiol. 54, 405–408, 1988), which is specifically associated with spoilage of vacuum-packed meats, has been isolated. It certainly would be of use in the dairy industry to have a quick and reliable method to identify and classify relevant strains of the lactic acid bacteria.

SUMMARY OF THE INVENTION

A first object of the present invention is to provide a specific DNA probe, which can be used in hybridisation procedures to specifically identify strains belonging to the *Lactobacillus delbrueckii* species, either in bacterial cultures, or as food constituents or during food processing, e.g. during industrial fermentation.

A second object of the present invention is to provide a process for producing such a specific DNA probe.

A third object of the present invention is to provide methods for specifically identifying strains belonging to the *L. delbrueckii* species with this DNA probe or with DNA parts thereof. To this end, firstly, the DNA probe according to the present invention comprises a DNA fragment lypridizes specifically to chromosomal DNA of strains of the *L.delbrueckii* species. This DNA fragment is preferably labeled by any suitable means, such as $^{32}P$, $^{35}S$ or biotin, for example. Preferably, this DNA fragment comprises an EcoRI fragment of chromosomal DNA from a strain of the *L.delbrueckii* species. Even more preferably this EcoRI fragment comprises a large open reading frame capable of complementation of a Leu minus lesion. Such a DNA fragment may be the 1633 base pair long EcoRI fragment of the plasmid pY85, for example.

Secondly, the process for producing a DNA probe according to the present invention comprises preparing an EcoRI clonebank from a strain of the *L.delbrueckii* species, transforming said EcoRI clonebank into a strain of *E.coli* having a Leu minus lesion, selecting for Leu plus clones, and isolating therefrom a clone of which an EcoRI DNA fragment is capable of hybridisation to chromosomal DNA of strains of the *L.delbrueckii* species.

Thirdly, a first method for identifying a bacterial strains of the *L.delbrueckii* species according to the present invention comprises preparing chromosomal DNA of a strain to be identified and checking whether this DNA hybridises to the present probe or to a probe produced by the present process.

A second method comprises preparing chromosomal DNA of a strain to be identified and carrying out a polymerase chain reaction on this DNA with parts of DNA sequences identical with parts of DNA sequences of the present probe or of a probe produced by the present process.

In preferred embodiments of these methods the chromosomal DNA is prepared by growing cells of the strain to be identified on a culture medium supplemented with a fermentable carbon source, incubating them in the presence of proteinases, treating them with an N-acetyl-muramidase, further incubating them in the presence of an emulsifying agent, a chelating agent and a proteinase, phenol extracting DNA therefrom, ethanol precipitating the extracted DNA, treating this DNA with an RNaSe and chloroform extracting the RNase treated DNA.

The above second method, preferably including the above preferred embodiment, is especially provided for identifying strains the cells of which are only present in a very low concentration in some substrates. On the other hand, the above first method, which has proven to be of a very high sensitivity, may even be used for carrying out identification tests on chromosomal DNA prepared by simply lysing cells of a strain to be identified, either from cultures or on solid supports such as e.g. filter paper or nitrocellulose paper.

Figure 1:
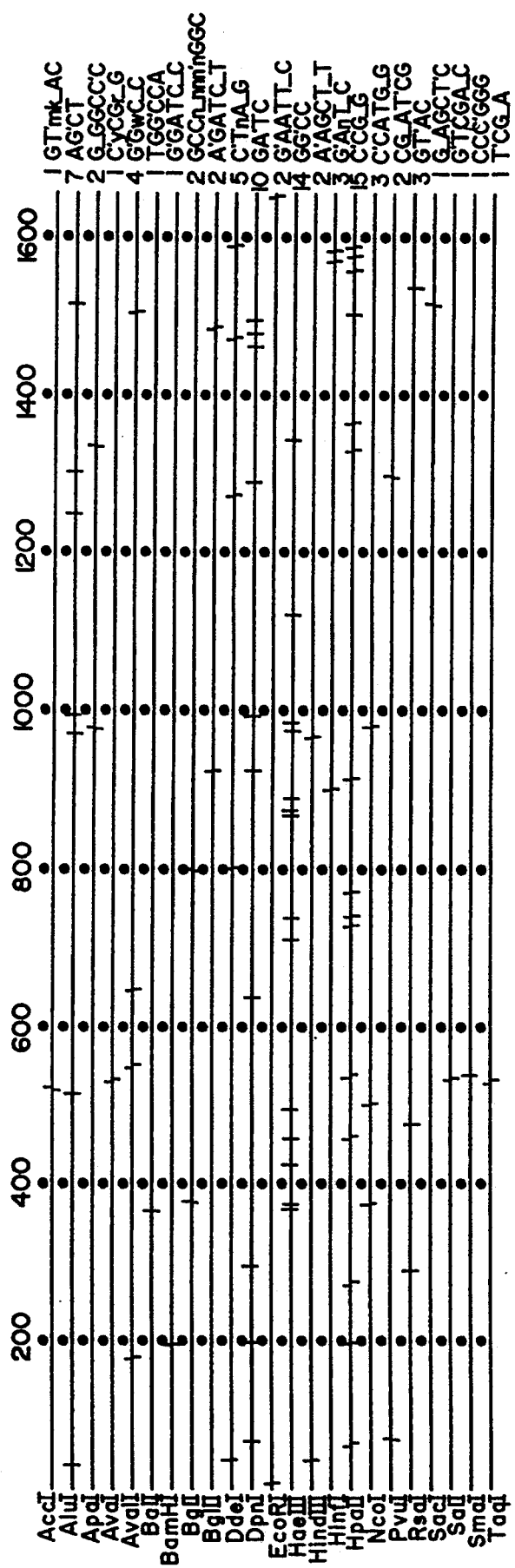
FIG. 1 is a restriction map of the EcoRI DNA fragment of the plasmid pY85.

The scale is indicated in base pairs (bp). Stickyend or bluntend restriction sites are indicated for each enzyme.

Enzymes that do not cut are:

BclI, ClaI, EcoRV, KpnI, MluI, NdeI, NruI, PstI, and PvuII.

DETAILED DESCRIPTION OF THE INVENTION

The plasmid pY85 was deposited pursuant to the Budapest Treaty on May 18, 1994, in the Collection Nationale de Cultures de Microorganismes (CNCM), Institut Pasteur, 28 rue du Dr. Roux, 75724 Paris Cedex 15, France, where it was given the number CNCM I-1419.

By transforming a clonebank of L.bulgaricus into GE891, it was possible to isolate individual clones, which can complement the Leu minus lesion of this E.coli strain. One of these clones, pY85, proved to be very useful as genetic probe in hybridisation assays to specifically identify the species of Lactobacillus delbrueckii. In screening experiments applying dot-blot hybridisation, over 30 different Lactobacillus strains from different origins were tested. It could be shown that pY85 only hybridised specifically to the L.delbrueckii species, ie. its subspecies bulgaricus, delbrueckii and lactis. No hybridisation to any other of the tested bacteria (table I) could be detected. In order to test the specificity of the present probe, the washing conditions of the dot-blots were lowered to room temperature (20° C.) and the SSC concentration were increased to 2XSSC. Even under these very low stringency conditions, it was absolutely not possible to find hybridisation of pY85 with any non L.delbrueckii species.

The sensitivity of pY85 to detect L.delbrueckii DNA was tested by hybridising it to serial dilutions of appropriate chromosomal DNA's. It was noted that with an over-night exposure of an X-ray film to a filter, it was possible to easily detect hybridisation to as little as 2pg of target DNA. Furthermore, hybridisation of subfragments of pY85, a 200bp and 500bp long fragment, to Lactobacillus was tested and identical results with respect to the complete fragment were found. It can therefore be concluded that any part of the pY85 fragment may be sufficient for specifically identifying L.delbrueckii. From these data it can furthermore be assumed, that the PCR (polymerase chain reaction) (Saiki et al., Science 230, 1350–1354, 1985; Saiki et al., Science 239, 487–491, 1988), which makes use of part of the pY85 DNA sequence, may work as well in identifying this specific Lactobacillus species. Because of its great amplification effect, the PCR method may be regarded as a very interesting possibility in cases where minute amounts of Lactobacillus bacteria have to be traced as for example in food samples.

DNA sequence analysis and further genetic analysis showed that the pY85 fragment is coding for a structural gene. As essential gene products are usually subject to selection of their functions, these genes are mostly good conserved regions of DNA. It is therefore likely that because of the structural function of the pY85 fragment, this piece of DNA serves as such a good, highly specific probe for the Lactobacillus delbrueckii species.

EXAMPLES

MATERIALS AND METHODS

Bacteria and plasmids

Lactic acid bacterial strains used in the Examples hereafter are shown in table I. E.coli strains are HB101 (leuB6 proA2 recA13 thi1 ara14 lacY1 galK2 xy15 mtl1 rpsL20 supE44 hsdS20) (H. W. Boyer et al., J.Mol.Biol. 41, 459–472, 1969) and GE891 (F⁻endA1 thi1 hsdR17 supE44 leu291 ilvD145) (G. Eggertsson, Institut of Biology, University of Iceland, Reykjavik, Iceland, unpublished). The plasmid used as vector was YRP17 (Hottinger et al., Mol.Gen. Genet. 188,219–224, 1982).

Media

For growth of the different Lactobacilli, Lactococci and Propionibacteria MRS broth (Difco Laboratories) was used, supplemented with 1% lactose. E.coli strains were grown in LB medium.

Preparation of DNA i) Chromosomal DNA from Lactobacillus, Lactococcus and Propionibacteria. Cells were diluted from overnight cultures into 10ml MRS, supplemented with 1% lactose and grown to mid-log phase at 43° C. The cells were then harvested by centrifugation, washed once in cold 1M NaCl, and incubated for 1h at 37° C. in the presence of Proteinase K (250 µg/ml) and Pronase E (500 µg/ml). The cells were washed in TE (10 mM Tris hydrochloride pH 7.4; 1mM EDTA) and treated with Mutanolysin (200 µg/ml) in the presence of TE for 1h at 37° C. SDS, EDTA and Proteinase K were added to a final concentration of 0.1%, 75 mM and 200µg/ml, resp., and incubated for 4h at 65° C. The DNA was then phenol extracted, ethanol precipitated and spooled onto a sterile toothpick. The DNA was resuspended in TE in the presence of RNase A (200 µg/ml), chloroform extracted, reprecipitated in ethanol and spooled again onto a toothpick. The DNA was then resuspended in 100 l of TE and stored at 4° C.

ii) Plasmid DNA from E.coli. Plasmid DNA from E.coli was isolated and as needed purified on CsCl gradient according to Maniatis et al. (Molecular cloning: a laboratory manual. Cold Spring Harbor Laboratory, Cold Spring Harbor, N.Y., 1982). Chemicals were purchased from E.Merck Chemicals Inc. and the enzymes from Sigma Chemical Co..

Construction of an EcoRI clonebank from Lactobacillus bulgaricus in YRP17

Chromosomal DNA from L.bulgaricus type was digested to completion with EcoRI and ligated into the vector YRP17, which had been previously linearised by cleavage at its unique EcoRI site and phosphatase treated. The ligation mixture was then transformed into HB101 and a representative number of about 20'000 colonies, 66% of which had insertions of a mean size of about 1.9 kb, were collected and amplified.

The enzymes were used according to the suppliers and transformation of E.coli was done according to Maniatis et al.

Selection for Leu⁻ Complementing Clones

The EcoRI clonebank had been transformed into GE891. In order to enrich for transformants, the culture had been first grown in LB medium containing 70 g/ml ampicillin over night at 37° C. The cells were then washed in minimal medium and appropriate dilutions were plated onto minimalagar plates containing isoleucine, valine and glucose in 20 µg/ml, 20 µg/ml and 1 mg/ml, respectively. The incubation was at 37° C. over night.

Labeling of DNA Fragments

To radioactively label the DNA, we used a fill-in-replacement DNA synthesis (Maniatis et al. ). The T4 DNA polymerase was purchased from Boehringer-Mannheim, [ -$^{32}$P]dATP from Amersham Co.

Hybridisation Procedures i) Dotblot hybridisation. Aliquots of 200ng of chromosomal DNA in TE were denatured by heating for 5 minutes at 95° C. SSC was added to the aliquots to give a final concentration of 16X SSC and then the mixture was spotted onto 20XSSC wetted GeneScreen paper and rinsed once with 20XSSC. A Bio-Rad dotblot apparatus was used. The filter was then ready for DNA hybridisation, applying standard procedures with hybridisation at 65° C. 6XSSC and a subsequent wash at 65° C. and 0,1XSSC (E. Southern, J. Mol. Biol. 98, 503–517, 1975). To detect the hybridisation signals, the filters were used to expose X-ray films.

ii) Southern-blot hybridisation. Southern-blot hybridisations were carried out according to standard procedures (E.Southern). Hybridisations and washes were at 65° C.

Restriction Mappiny and DNA Sequencing

Restriction enzymes were purchased from Boehringer-Mannheim Co. and New England Biolabs Co. and were used as recommended by the suppliers. DNA sequencing was performed by the chain termination reaction method using M13phage derivates (F.Sanger et al., J.Mol.Biol. 94, 441–448, 1975; F.Sanger et al., Proc.-Natl.Acad. Sci. 74, 5463–5467, 1977; J.Messing et al., Gene 19, 269–276, 1982).

EXAMPLE 1

1.1.

Isolation of GE891 Leu$^-$ Complementing Clones from Lactobacillus

EcoRI digested chromosomal DNA of L.bulgaricus NCDO 1489 has been used to establish a clonebank in vector YRP17. This clonebank served to transform GE891, as described above. Several individual colonies which were growing on the minimalagar plates were isolated and analysed. In order to exclude spontaneous leu291 revertants from the screening, plasmid DNA of these colonies was isolated and used for retransforming GE891, with subsequent selection on the aminoacid substituted minimal agar plates. A high frequency of complementation of the leu291 lesion of GE891 in this second transformation indicated that the complementing factor is located on the plasmid. One of the clones isolated in this way is pY85.

1.2

Restriction Mapping and DNA Sequencing

A restriction map of pY85 was determined using several restriction enzymes. For a more detailed investigation, however, the entire DNA sequence of the EcoRI fragment of pY85 has been determined. An analysis of the DNA sequence showed that the fragment contains one large open reading frame which is responsible for the complementation of the Leu minus mutation. By means of the DNA sequence, a more detailed restriction map of the 1633 basepair long EcoRI fragment of pY85 could be generated. It is shown in FIG. 1.

1.3

Specificity and Sensitivity of the Probe pY85

Hybridisation of the EcoRI fragment of pY85 as probe on Southern-blots against genomic DNA of the L.bulgaricus type strain NCDO 1489 showed that a single allelic gene had been isolated. However, it was observed that not all Lactobacillus strains hybridised to the probe. Therefore pY85 was tested against different representatives of the Lactobacillus genus and some other lactic acid bacteria with dot-blot hybridisations. As probes for these tests the $^{32}$p labeled EcoRI fragment of pY85 was used. A summary is presented in Table I.

TABLE I

| CRN[a] code | Bacterial strains | | signal[b] with pY85 |
|---|---|---|---|
| | source | species | |
| LB1 | CRN collection | L. bulgaricus | + |
| LB2 | " | " | + |
| LB6 | " | " | + |
| LB9 | " | " | + |
| LB12 | " | " | + |
| LB32 | " | " | + |
| LB34 | " | " | + |
| LB57.1 | " | " | + |
| LB81.4 | " | " | + |
| LB92.9 | " | " | + |
| N52 | NCDO 1006 | " | + |
| N95 | NCDO B 15 | " | + |
| N123 | NCDO 1489 | L. bulgaricus type | + |
| N124 | ATCC 21815 | L. bulgaricus | + |
| N141 | Piacenza CO 14 | " | + |
| N5 | ATCC 12315 | L. lactis type | + |
| N9 | Liebefeld 125 | " | + |
| N62 | NCDO 270 | " | + |
| N8 | NCIB 8130 | L. delbrueckii type | + |
| N187 | ATCC 9649 | " | + |
| LD1 | CRN collection | " | + |
| LB14 | " | L. helveticus | − |
| LB15 | " | " | − |
| LB20 | " | " | − |
| N2 | ATCC 15009 | L. helveticus type | − |
| N6 | NCDO 87 | " | − |
| N106 | NCDO 2395 | " | − |
| N213 | Piacenza b 50 | " | − |
| N7 | NCDO 1750 | L. fermentum | − |
| N27 | ATCC 393 | L. casei type | − |
| N25 | ATCC 4005 | L. buchneri | − |
| N24 | ATCC 8041 | L. plantarum | − |
| N207 | ATCC 27865 | L. maltaromicus | − |
| N26 | ATCC 14869 | L. brevis | − |
| N12 | ATCC 4356 | L. acidophilus | − |
| N211 | DSM 20016 | L. reuteri type | − |
| N50 | ATCC 12278 | L. sp. | − |
| N51 | ATCC 13866 | L. sp. | − |
| SL9 | CRN collection | Lactococcus lactis | − |
| ST1 | " | Lactococcus thermophilus | − |
| PP13 | " | Propionibac.shermanii | − |
| PP21 | " | Propionibac freudenreichii | − |
| HB101 | " | E. coli | − |

[a]NestléResearch Centre
[b]with dotblot hybridisation

The hybridisation results show that pY85 specifically only lights up DNA from the Lactobacillus delbrueckii strains, subspecies bulgaricus, delbrueckii and lactis. All other tested strains of different Lactobacillus species, of Lactococcus and Propionibacteria were negative.

EXAMPLE 2

The two NcoI fragments of 200 bp and 500 bp length from the pY85 clone (FIG. 1) were isolated and used in the way disclosed in Example 1 as probes for the hybridisation. It was observed that the same high specific hybridisation was obtained with these shorter probes.

EXAMPLE 3

In order to test the sensitivity of the dot-blot test carried out in Examples 1 and 2, serial dilutions of *L. lactis* type chromosomal DNA were made and the diluted DNA was then hybridised with the pY85 EcoRI fragment. A positive signal could easily be detected at 1 pg of target DNA. Furthermore, hybridisation was tested under less stringent washing conditions using the different Lactobacillus strains against the pY85 probe. After washing in 2XSSC at 20° C., it was only possible to detect a signal of hybridisation with the DNA of the *Lactobacillus delbrueckii* species. For the Lactobacillus screening according to Examples 1 and 2, however, at least 200 ng of DNA per sample and stringent washing conditions were used.

We claim:

1. The plasmid pY85.
2. An isolated EcoRI DNA fragment, or NCOI subfragment thereof, of the plasmid pY85.
3. An isolated NcoI subfragment of the EcoRI fragment of claim 2.
4. A fragment according to claim 2 or 3 which is detectably labelled.
5. A process for identifying bacterial strains of the *L. delbrueckii* species comprising preparing chromosomal DNA of a strain to be identified and determining whether the prepared chromosomal DNA hybridizes to the plasmid pY85 or to an EcoRI DNA fragment, or NCOI subfragment thereof, of the plasmid pY85, wherein hybridization identifies the presence of a strain of the *L. delbrueckii* species.
6. A process according to claim 5 wherein it is determined whether the plasmid pY85 hybridizes to the prepared chromosomal DNA.
7. A process according to claim 5 wherein it is determined whether an EcoRI fragment of the plasmid pY85 hybridizes to the prepared chromosomal DNA.
8. A process according to claim 5 wherein it is determined whether an NCoI subfragment of the EcoRI fragment hybridizes to the prepared chromosomal DNA.

* * * * *

UNITED STATES PATENT AND TRADEMARK OFFICE
CERTIFICATE OF CORRECTION

PATENT NO. : 5,429,924
DATED : July 4, 1995
INVENTOR(S) : Michele DELLEY, et al.

It is certified that error appears in the above-indentified patent and that said Letters Patent is hereby corrected as shown below:

On the title page, in item [75] Inventors (left column), "Mich';acu*e*le" should be --Michele--.

On the tile page, right column, in the identification of the last-listed PUBLICATION, change "Saika" to --Saiki--.

Column 2, line 8, change "lybridizes" to --hybridizes--.

UNITED STATES PATENT AND TRADEMARK OFFICE
CERTIFICATE OF CORRECTION

PATENT NO. : 5,429,924    Page 2 of 2
DATED : July 4, 1995
INVENTOR(S) : Michele DELLEY, et al.

It is certified that error appears in the above-indentified patent and that said Letters Patent is hereby corrected as shown below:

In each of column 7, line 22 (line 1 of claim 2) and column 8, line 10 (line 6 of claim 5), change "NCOI" to --NcoI--.

Signed and Sealed this

Twenty-sixth Day of September, 1995

Attest:

BRUCE LEHMAN

*Attesting Officer*   Commissioner of Patents and Trademarks